United States Patent [19]
van Loveren et al.

[11] Patent Number: 4,585,582
[45] Date of Patent: Apr. 29, 1986

[54] PERFUMERY USES OF 2-N-PENTYL-2-CYCLOHEXEN-1-ONE

[75] Inventors: Augustinus G. van Loveren, Ryebrook, N.Y.; Mark A. Sprecker, Sea Bright, N.J.

[73] Assignee: International Flavors & Fragrances Inc., New York, N.Y.

[21] Appl. No.: 709,917

[22] Filed: Mar. 8, 1985

[51] Int. Cl.$^4$ .............................................. A61K 7/46
[52] U.S. Cl. .............................. 252/522 R; 252/8.6; 252/174.11; 252/522 A; 424/69; 424/70
[58] Field of Search ............... 252/8.6, 174.11, 522 R, 252/522 A; 424/69, 70

[56] References Cited

U.S. PATENT DOCUMENTS

| | | | |
|---|---|---|---|
| 3,823,190 | 7/1974 | Oberhänsli | 252/522 R X |
| 4,217,251 | 8/1980 | Dastur | 252/522 R |
| 4,246,292 | 1/1981 | Könst et al. | 252/522 R X |
| 4,310,701 | 1/1982 | Wilson et al. | 568/347 |
| 4,326,997 | 4/1982 | Willis et al. | 252/522 R |
| 4,352,943 | 10/1982 | Kaiser et al. | 252/522 R X |

FOREIGN PATENT DOCUMENTS 0099546  6/1982  Japan .............................. 252/522 R

OTHER PUBLICATIONS

Bernard, ed., *Flavor and Fragrance Materials*—1985, pp. 184–185, Allured Publishing Corp.
Arctander, *Perfume and Flavor Chemicals*, vol. II (1969), Monograph 2457.

*Primary Examiner*—Thomas A. Waltz
*Attorney, Agent, or Firm*—Arthur L. Liberman

[57] ABSTRACT

Described is 2-n-pentyl-2-cyclohexen-1-one having the structure:

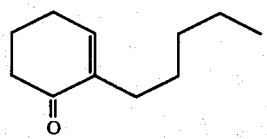

useful in augmenting or enhancing the aroma of consumable materials including perfume compositions, colognes, and perfumed articles including solid or liquid anionic, cationic, nonionic or zwitterionic detergents, fabric softeners, fabric softener articles as well as hair sprays, shampoos, bath oils and perfumed polymers.

5 Claims, No Drawings

PERFUMERY USES OF 2-N-PENTYL-2-CYCLOHEXEN-1-ONE

BACKGROUND OF THE INVENTION

The instant invention relates to 2-n-pentyl-2-cyclohexen-1-one having the structure:

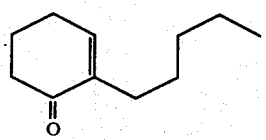

and uses thereof in augmenting or enhancing the aroma of consumable materials.

Materials which can provide muguet, orange, coconut, lactonic and jasmine-like aroma nuances are well known in the art of perfumery. Many of the natural substances which provide such fragrances and contribute the desired nuances to perfumery compositions are high in cost, vary in quality from one batch to another and/or are generally subject to the usual variations of natural products.

The compound having the structure:

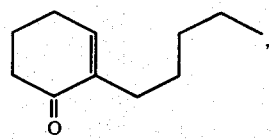

the 2-n-pentyl-2-cyclohexen-1-one of our invention, is shown to be useful as a synthesis intermediate in preparing esters useful in perfumery having the structure:

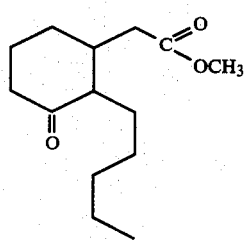

in U.S. Pat. No. 4,310,701 issued on Jan. 12, 1982, the specification for which is incorporated by reference herein.

Arctander "Perfume and Flavor Chemicals (Aroma Chemicals) II" at monograph 2457 describes a possible precursor of the 2-n-pentyl-2-cyclohexen-1-one of our invention having the structure:

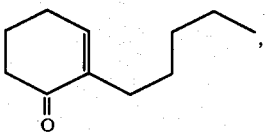

which precursor is 2-n-pentylidene-cyclohexanone-1 having the structure:

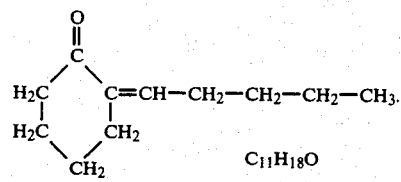

Arctander states that this compound is warm and slightly spicy, having a jasmine odor of excellent tenacity. Arctander further states that this compound is "less floral than the most popular iso-Jasmones . . . "

Arctander "Perfume and Flavor Chemicals (Aroma Chemicals)" Vol. I at monograph 1789 describes "iso-Jasmone" as follows:

"Commercial products under this name are mixtures of several isomer ketones of which:
(1) n-Hexyl-cyclopenten-2-one: is described under DIHYDRO-iso-JASMONE. No. 955.
(2) n-Hexylidene cyclopentanone: is described under alpha-HEXYLIDENE CYCLOPENTANONE. No. 1670.
(3) 1-n-HEXYL-2-CYCLOPENTEN-1-ONE, so-called Dihydrojasmone. No. 1659.

The literature has been very illogical and inconsistent on the subject of nomenclature, identity and odor description of the commercially available iso-Jasmones, etc.

One of the main points of disagreement seems to be the preference of isomer (2) as compared to one or more of the isomers which have an unsaturated ring and a saturated side chain.

Yet, it has also been claimed that the hydrogenated product (which may be identical even when prepared from two different unsaturated isomers) has a superior odor.

The author finds that personal opinions on the odor of these materials will not contribute constructively to the problem, and only general odor descriptions are therefore listed.

"iso-Jasmone" is a name given to commercial products of very widely different composition. The fact that there are several "price-levels" also emphasize the difference in opinion as to which odor is closest to that of natural Jasmone, and which is the most desirable for general perfumery use.

Although iso-Jasmone is quoted in literature with a chemical structure formula, commercial products are components, some iso-Jasmones have more than four major components.

Iso-Jasmones are used widely in perfumes and flavors, and the very attractive cost of certain isomer blends has contributed to an extensive use of these ketones in quite ordinary perfumes, not just reserved for the finest or most costly compositions.

Various effects can be achieved with various types of iso-Jasmone: floral, fruity, minty, warm, diffusive, "lifting", oily, ets. but with respect to Jasmine similarity, they are all inferior to cis-Jasmone . . . "

At monograph 1659, Arctander describes for use in perfumery 2-n-hexyl-2-cyclopenten-1-one having the structure:

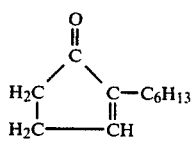

as "Powerful fruity-green, oily and somewhat floral odor of moderate tenacity."

Nothing in the prior art, however, expressly or implicity states the unexpected, unobvious and advantageous perfumery properties of the 2-n-pentyl-2-cyclohexen-1-one having the structure:

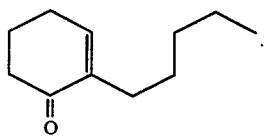

THE INVENTION

The present invention provides the 2-n-pentyl-2-cyclohexen-1-one having the structure:

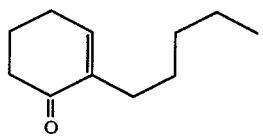

for its organoleptic properties in augmenting or enhancing the organoleptic properties of consumable materials, that is the aroma of perfumes, colognes and perfumed articles (such as perfumed polymers, solid or liquid anionic, cationic, nonionic or zwitterionic detergents, soaps, fabric softener compositions, dryer added fabric softener articles such as BOUNCE ® (registered trademark of the Procter & Gamble Co. of Cincinnati, Ohio), fabric brighteners, cosmetic powders, bath preparations and hair preparations such as hair sprays and shampoos).

The 2-n-pentyl-2-cyclohexen-1-one of our invention having the structure:

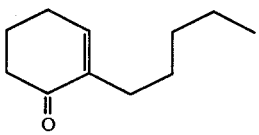

is prepared in accordance with the process set forth in U.S. Pat. No. 4,310,701 issued on Jan. 12, 1982 the disclosure of which is incorporated by reference herein.

Firstly, an aldol condensation reaction takes place between cyclohexanone and n-pentanal according to the reaction:

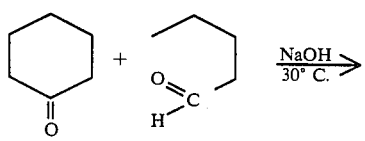

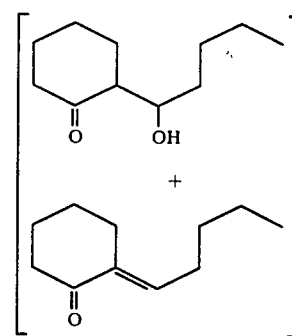

The aldol condensation reaction may take place at a temperature of between 20° C. and 50° C. over a period of time of from about one half hour up to four fours. Preferably, the reaction time is about one hour and the reaction temperature is about 30° C. The mole ratio of cyclohexenone:pentanal may vary from about 3:1 up to about 1:3 with a preferred mole ratio of 1.8 moles of cyclohexenone:1 mole of pentanal. The mole ratio of base used (e.g., sodium hydride, barium hydroxide or potassium hydroxide):aldehyde may vary from about 0.05 moles base:1 mole aldehyde up to 0.1 mole base:1 mole aldehyde with a preferred mole ratio of 0.083:1.

The reaction of the resulting aldol condensation product to form the compound having the structure:

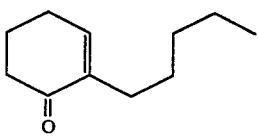

is, in fact, two reactions, the first reaction a one step reaction, to wit:

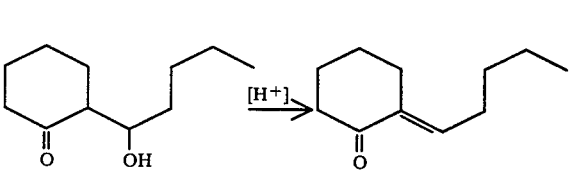

and

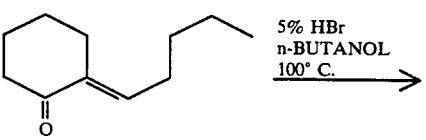

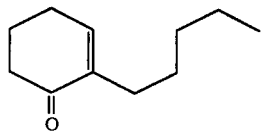

which can also be shown thusly:

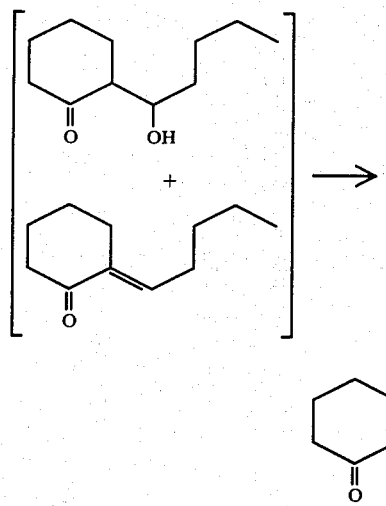

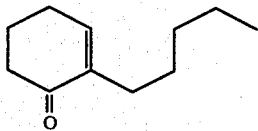

The reaction can either be performed step wise via the alkylidene cyclopenenone by means of dehydration with an acid such as oxalic acid followed by endoisomerization with aqueous acid (hydrochloric acid or hydrobromic acid) in refluxing n-butanol or, more preferably, reacting the aldol condensation product itself with hydrogen chloride or hydrogen bromide, preferably, hydrogen bromide in refluxing n-butanol. As will be seen by the examples, using an acid such as para-toluene sulfonic acid fails to give rise to an appreciable yield compared with the use of hydrogen chloride or hydrogen bromide.

The 2-n-pentyl-2-cyclohexen-1-one of our invention having the structure:

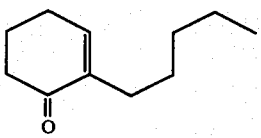

can be used to contribute muguet, orange, coconut, lactonic and jasmine-like aroma nuances to perfume compositions, perfumed articles such as solid or liquid anionic, cationic, nonionic or zwitterionic detergents, perfumed polymers (e.g., perfumed polyethylene, perfumed polypropylene and perfumed poly(epsilon caprolactone), fabric softener compositions, fabric softener articles, optical brighteners, fabric conditioners, hair preparations, shampoos and hair sprays). As olfactory agents, the 2-n-pentyl-2-cyclohexen-1-one of our invention can be formulated into or used as a component of a "perfume composition".

The term "perfume composition" is used herein to mean a mixture of organic compounds including, for example, alcohols, aldehydes, ketones other than the 2-n-pentyl-2-cyclohexen-1-one of our invention, nitriles, ethers, lactones, esters and frequently hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, the individual component will contribute its particular olfactory characteristics, but the overall effect of the perfume composition will be the sum of each of the effects of each of the ingredients. Thus, the 2-n-pentyl-2-cyclohexen-1-one of this invention can be used to alter the aroma characteristics of the perfume composition, for example, by highlighting or moderating the olfactory reaction contributed by another ingredient in the composition.

The amount of 2-n-pentyl-2-cyclohexen-1-one of our invention having the structure:

which will be effective in perfume compositions depends upon many factors including the other ingredients, their amounts and the effects which are desired. It has been found that perfume compositions containing as little as 0.1% of the 2-n-pentyl-2-cyclohexen-1-one of our invention or even less in perfume compositions containing as much as 70% of the 2-n-pentyl-2-cyclohexen-1-one of our invention can be used to impart interesting muguet, orange, coconut, lactonic and jasmine-like aroma nuances to perfumed articles, perfume compositions and colognes. Such perfumed articles include fabric softener compositions, dryer-added fabric softener articles, cosmetic powders, talcs, solid and liquid anionic, cationic, nonionic or zwitterionic detergents and perfumed polymers. The amount employed can range up to 70% and will depend on consideration of cost, nature of the end product and the effect desired on the finished product and particular fragrance sought.

Thus, the 2-n-pentyl-2-cyclohexen-1-one of our invention can be used alone or in a perfume composition as an olfactory component in solid or liquid anionic, cationic, nonionic or zwitterionic detergents (including soaps), perfumed polymers (those which are microporous and those which are macroporous) and those which contain particulate absorbent fillers such as talc and calcium carbonate), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer, a macroporous polymer, a polymer containing an absorbent filler or a solid or liquid anionic, cationic, nonionic or zwitterionic detergent, or a cosmetic powder, as little as 0.01% of the 2-n-pentyl-2-cyclohexen-1-one of our invention will suffice to provide interesting muguet, orange, coconut, lactonic and jasmine-like aromas. Generally, no more than 0.8% of the 2-n-pentyl-2-cyclohexen-1-one of our invention is required. Thus, the range of the 2-n-pentyl-2-cyclohexen-1-one of our invention operable in perfumed articles of our invention is from about 0.01% up to about 0.8%.

In addition, the 2-n-pentyl-2-cyclohexen-1-one of our invention can contain a vehicle or carrier. The vehicle can be a liquid such as an alcohol such as ethanol, a glycol such as propylene glycol or the like. The carrier can be an absorbent solid such as a gum (e.g., xanthan gum, guar gum or gum arabic) or components for encapsulating the solvent such as by coacervation using gelatin or such as by polymerization around a liquid center as by polymerizing a urea formaldehyde prepolymer around a liquid perfume center.

The 2-n-pentyl-2-cyclohexhen-1-one of our invention is blended into polymers when forming a perfumed polymer by means of extrusion using a single or double screw extruder or techniques such as those set forth in U.S. Pat. No. 4,247,498 issued on Jan. 27, 1981 which discloses microporous polymers which are capable of containing volatile substances such as perfumes and the like and forms ranging from films to blocks in intricate shapes from synthetic thermoplastic polymers such as olefinic condensation or oxidation polymers. The specification of U.S. Pat. No. 4,247,498 is incorporated herein by reference. Other techniques of blending the 2-n-pentyl-2-cyclohexen-1-one of our invention with the polymers are specified in U.S. Pat. No. 3,505,432 (the specification for which is incorporated by reference herein) which discloses a method for scenting a polyolefin with such materials as the 2-n-pentyl-2-cyclohexen-1-one of our invention which comprises:

(a) Mixing a first amount of a liquid polyolefin, e.g., polyethylene or polypropylene with a relatively large amount of scent imparting material (in this case the 2-n-pentyl-2-cyclohexen-1-one of our invention) to form a flowable mass;

(b) Forming drops of said mass and causing substantially instantaneous solidification of said drops into polyolefin pellets having a relatively large amount of such scent imparting materials as the 2-n-pentyl-2-cyclohexen-1-one of our invention imprisoned therein;

(c) Melting the pellets with a second amount of said polyolefin said second amount being larger than said first amount; and (d) Solidifying the melt of (c).

The following examples set forth processes for preparing the 2-n-pentyl-2-cyclohexen-1-one of our invention. Example III and the following examples set forth the methods for utilizing the 2-n-pentyl-2-cyclohexen-1-one of our invention for its organoleptic properties.

Unless otherwise indicated, all parts and percentages herein are by weight.

EXAMPLE I-A

Reaction:

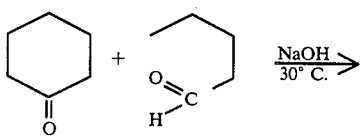

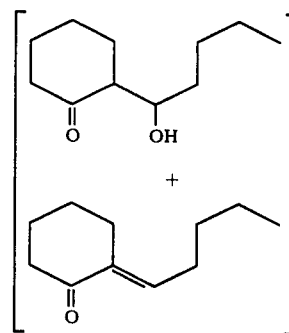

Reaction:

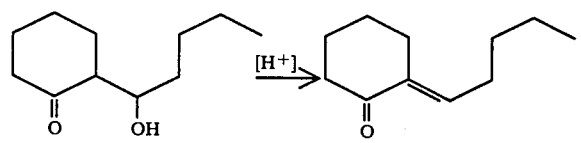

Into a 5-liter reaction flask equipped with mechanical stirrer, 500 ml addition funnel, immersion thermometer and reflux condenser and 5-liter heating mantle and dry ice/isopropyl alcohol bath are charged 16.5 grams of sodium hydroxide and 1500 ml water. The resulting mixture is warmed to 30° C. 882 grams (9.0 moles) of cyclohexanone is then added dropwise with stirring over a 15 minute period while maintaining the reaction temperature at 30° C. with the dry ice/isopropanol bath.

430 grams (5.0 moles) of n-valeraldehyde is then added dropwise with stirring over a 40 minute period while keeping the temperature at 30° C. After addition, the reaction mass is stirred for a period of 1 hour at 30° C.

After 1 hour, 30.0 grams of acetic acid is added using a dropping pipette and the reflux condenser is replaced with a splash column equipped with rush-over head. The resulting mixture is then heated and steam distilled. All fractions are monitored on a 400′ SE-30 glass capillary GLC column. The distillation is shut down when no further apparent oil layer is formed. The resulting mixture is allowed to cool down and poured into a separatory funnel. The aqueous layer is separated and washed with two volumes of toluene. The toluene layer is combined with the organic layer and the resulting organic layer is washed with two volumes of saturated sodium chloride solution and then filtered through cotton. The resulting material is placed in the 5-liter reaction flask as equipped above.

10.0 grams of oxalic acid is then added and the reaction mixture is heated with stirring and azeotropically distilling water until no further water is evolved (about 90 ml water being removed). The reaction equipment is then shut down and the reaction mass is cooled and poured into a 4-liter separatory funnel. The reaction mass is then washed with two volumes of saturated sodium chloride solution followed by two volumes of 5% sodium carbonate solution followed by two volumes of saturated sodium chloride solution. The resulting material is then dried over anhydrous sodium sulfate and concentrated to yield 1120.0 grams of material.

The resulting product is then distilled under vacuum using a splash column and rush-over head.

EXAMPLE I-B

Reaction:

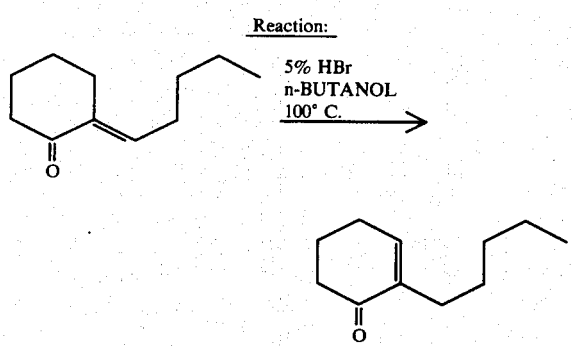

Into a 5-liter reaction flask equipped with mechanical stirrer, immersion thermometer, bubble condenser and 5-liter heating mantel are charged 581.3 grams (3.75 moles) of 2-pentylidene cyclohexanone prepared according to Example I-A and 2400 ml of 5% hydrogen bromide in n-butanol (120 ml hydrogen bromide in 2280 ml n-butanol). The resulting mixture is heated with stirring to reflux at 105° C. The reaction mass is then stirred over a period of 115 minutes while monitoring the progress on a 6'×¼" glass SE-30 packed column (operated at 150° C. isothermal) approximately every 5-10 minutes.

After 115 minutes, the reaction apparatus is shut down and the reaction mass is cooled. The resulting mixture is poured into a separatory funnel and washed with 1 volume of saturated sodium chloride solution followed by 1 volume of 10% sodium carbonate solution and 2 volumes of saturated sodium chloride solution. The resulting material is then dried over anhydrous sodium sulfate and concentrated to yield 795 grams of crude product. The resulting crude is then distilled under vacuum using a splash column and rush-over head.

EXAMPLE II-A

Reaction:

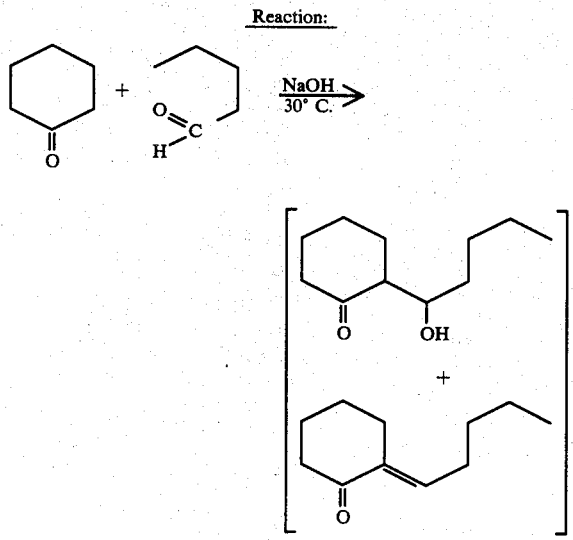

Into a 500 ml reaction flask equipped with mechanical stirrer, immersion thermometer, 150 ml addition funnel, water-cooled condenser, heating mantle and ice bath is placed 1.65 grams of sodium hydroxide pellets and 155 ml water. The resulting solution is warmed to 30° C. 75.6 grams (0.9 moles) of cyclohexanone is then added dropwise with stirring while maintaining the temperature at 30°-31° C. 43.0 grams (0.5 moles) of n-valeraldehyde is then added dropwise with stirring over a period of about 30 minutes while maintaining the temperature at 30° C. The reaction mass is then stirred for 1 hour at 30° C. At this point, 3.0 grams of acetic acid and 100 ml of water are added. The condenser is then replaced with a splash column and rush-over head and the reaction mass is heated to 95° C. to distill the unreacted cyclohexanone. The reaction mass is then distilled until the head temperature is 100° C. and the majority of the cyclohexanone is removed. The reaction apparatus is then shut down and the reaction mass is cooled and poured into a separatory funnel.

The oil layer is taken up in diethyl ether and separated form the aqueous layer. It is then washed with 1 volume of saturated sodium chloride solution and dried over anhydrous sodium sulfate and concentrated to yield 72.52 grams of crude product.

EXAMPLE II-B

Reaction:

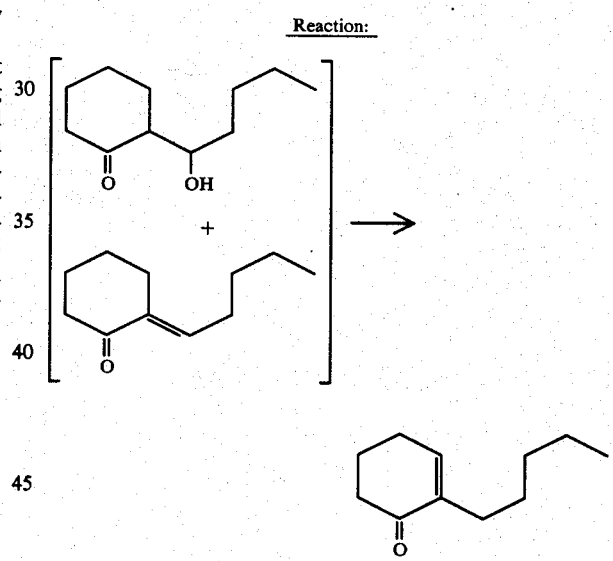

Into a 250 ml reaction flask equipped with mechanical stirrer, immersion thermometer, water-cooled condenser and heating mantel are charged 0.25 moles of the aldol condensation product produced according to Example II-A and 138.6 ml of 5% hydrogen bromide in n-butanol (6.60 ml of 48% of HBr in 132 ml of n-butanol). The reaction mixture is heated to reflux (102° C.) and maintained at reflux (monitoring by GLC) until all of the isomer having the structure:

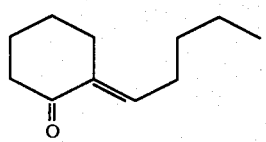

is isomerized to the product having the structure:

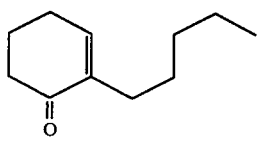

The ratio of endo:exo is about 14:1. The reaction apparatus is then shut down and the reaction mass is cooled and poured into a separatory funnel. The oil layer is then washed with 1 volume of saturated sodium chloride solution; followed by 1 volume of 10% sodium carbonate solution; followed by 3 volumes of saturated sodium chloride solution. The resulting material is then dried over anhydrous sodium sulfate and the crude material (172 grams) is distilled under vacuum. The yield is 140 grams.

EXAMPLE II-C

Reaction:

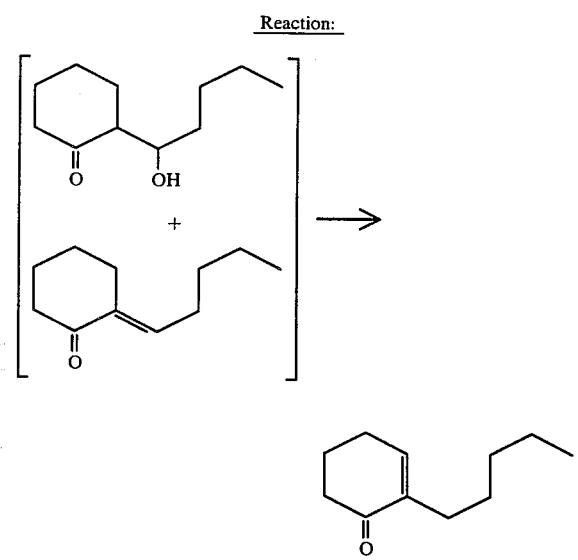

Into a 250 ml reaction flask equipped with mechanical stirrer, immersion thermometer, water-cooled condenser and heating mantle is placed 0.23 moles of the aldol condensation product of cyclohexanone and n-valeraldehyde produced according to Example II-A and 176.4 ml of 5% hydrogen chloride in n-butanol (8.4 ml of 38% HCl in 168 ml n-butanol). The reaction mass is heated with stirring to reflux and refluxed until a ratio of endo:exo isomer is about 13:1 monitored on a 6'×¼" SE-30 glass packed GLC column. The time of reaction of 170 minutes. At the end of the 170-minute period the reaction apparatus is shut down and the reaction mass is washed with 1 volume of saturated sodium chloride solution followed by 1 volume of 10% sodium carbonate solution and 3 volumes of saturated sodium chloride solution. The product is then dried over anhydrous sodium sulfate to yield 230 grams of crude. The crude material is distilled under vacuum using a rush-over head. The yield of product is 140 grams.

EXAMPLE II-D

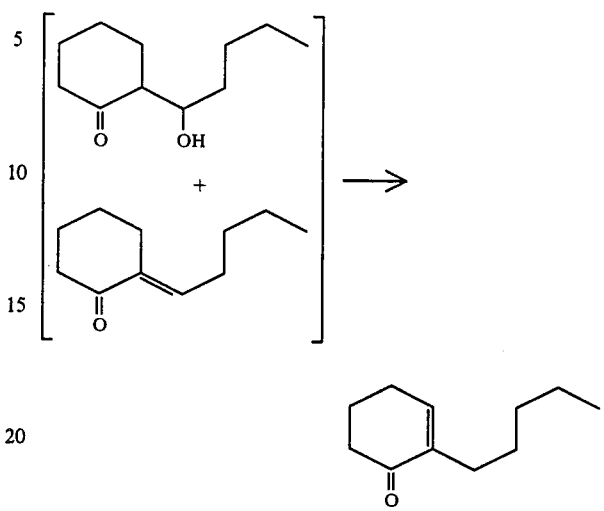

Into a 250 ml reaction flask equipped with mechanical stirrer, Dean-Stark trap with Freidrich's condenser, immersion thermometer and heating mantle is placed 20.0 grams of the cyclohexanone-n-valeraldehyde aldol condensation product produced according to Example II-A; 100 ml toluene and 2.28 grams (0.012 moles) of paratoluene sulfonic acid. The reaction mass is heated to reflux (114° C.) with stirring and approximately 2.6 ml water is azeotropically distilled from the reaction mass. The reaction is carried on for about 140 minutes and then the apparatus is shut down overnight for a period of 12 hours. The reaction is then restarted and run for 120 minutes additional time. The reaction mass is monitored on a 6'×¼" SE-30 GLC column until sufficient conversion appears to take place (about 13:1 endo:exo). The apparatus is shut down and the reaction product is cooled to room temperature.

The reaction product is washed with 1 volume of saturated sodium chloride solution; 2 volumes of 5% sodium carbonate solution; and 2 volumes of saturated sodium chloride solution. The product is then dried over anhydrous sodium sulfate and concentrated to yield 20.0 grams of crude material. The crude product is then rush-over distilled under vacuum yielding 11.1 grams of final product.

EXAMPLE III

Jasmine Perfume

The following mixture is prepared:

| INGREDIENT | PARTS BY WEIGHT |
|---|---|
| Para Cresol | 1 |
| Acetyl Methyl Anthranilate | 20 |
| Farnesol | 4 |
| Cis-3-hexenyl benzoate | 30 |
| Nerolidol | 30 |
| Indol | 15 |
| Eugenol | 20 |
| Benzyl Alcohol | 40 |
| Methyl Linoleate | 40 |
| Jasmine Lactone | 20 |
| Dihydromethyl Jasmonate | 10 |
| Linalool | 150 |
| Benzyl Acetate | 400 |
| Abietyl Alcohol | 150 |
| 2-n-pentyl-2-cyclohexen-1-one | 50 |

| INGREDIENT | PARTS BY WEIGHT |
|---|---|
| -continued | |
| (produced according to either of Examples I-B, II-B, II-C or II-D) | |

The 2-n-pentyl-2-cyclohexen-1-one of our invention imparts to this jasmine formulation a much more realistic natural-like jasmine flower aroma with intense muguet, orange, coconut and lactonic undertones. Accordingly, this perfume composition can be described as "natural jasmine flower-like with muguet, orange, coconut and lactonic undertones".

EXAMPLE VI

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| SUBSTANCE | AROMA DESCRIPTION |
|---|---|
| 2-n-pentyl-2-cyclohexen-1-one | A muguet, orange, coconut, lactonic and jasmine-like aroma profile. |
| Perfume composition of Example III | A natural jasmine flower-like aroma with muguet, orange, coconut and lactonic undertones. |

EXAMPLE V

Perfumed Liquid Detergents

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

Preparation of Colognes and Handkerchief Perfumes

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

Preparation of Soap Compositions

One hundred grams of soap chips (per sample) (IVORY ®, produced by the Procter & Gamble Company of Cincinnati, Ohio), are each mixed with one gram samples of substances as set forth in Table I of Example IV until homogeneous compositions are obtained. In each of the cases the homogeneous compositions are heated under 8 atmospheres pressure at 180° C. for a period of three hours and the resulting liquids are placed into soap molds. The resulting soap cakes, on cooling, manifest aromas as set forth in Table I of Example IV.

EXAMPLE VIII

Preparation of Solid Detergent Compositions

Detergents are prepared using the following ingredients according to Example I of Canadian Pat. No. 1,007,948 (incorporated by reference herein):

| INGREDIENT | PERCENT BY WEIGHT |
|---|---|
| Neodol ® 45-11 (a $C_{14}$–$C_{15}$ alcohol ethoxylated with 11 moles of ethylene oxide) | 12 |
| Sodium Carbonate | 55 |
| Sodium Citrate | 20 |
| Sodium Sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
   57% $C_{20-22}$HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example IV, supra.

EXAMPLE X

Hair Spray Formulation

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| INGREDIENTS | PARTS BY WEIGHT |
| --- | --- |
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America) | 0.03 weight percent |
| One of the perfumery substances as set forth in Table I of Example IV | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

What is claimed is:

1. A process for augmenting or enhancing the aroma of a consumable material selected from the group consisting of perfume compositions, colognes and perfumed articles comprising the step of intimately admixing with a perfume composition base, a cologne base or a perfumed article base, an aroma augmenting or enhancing quantity of the 2-n-pentyl-2-cyclohexen-1-one having the structure:

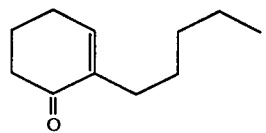

in recovered form.

2. The process of claim 1 wherein the consumable material is a perfumed article and the perfumed article is a solid or liquid anionic, cationic, nonionic or zwitterionic detergent.

3. The process of claim 1 wherein the consumable material is a perfume composition or a cologne.

4. The process of claim 1 wherein the consumable material is a perfumed article and the perfumed article is a drier-added fabric softener article or a fabric softener composition.

5. The process of claim 1 wherein the consumable material is a perfumed polymer.

* * * * *